(12) United States Patent
Carter et al.

(10) Patent No.: US 6,599,496 B2
(45) Date of Patent: *Jul. 29, 2003

(54) ENDOSCOPY TISSUE STAIN

(75) Inventors: Frank C. Carter, Wormleysburg, PA (US); Frank W. Jackson, Mechanicsburg, PA (US); Robert G. Whalen, Willington, CT (US)

(73) Assignee: Chek-Med Systems, Inc., Camp Hill, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/894,992

(22) Filed: Jun. 28, 2001

(65) Prior Publication Data

US 2002/0031474 A1 Mar. 14, 2002

Related U.S. Application Data

(63) Continuation-in-part of application No. 09/303,164, filed on Apr. 30, 1999, now Pat. No. 6,280,702.

(51) Int. Cl.$^7$ ................................................ A61K 49/00
(52) U.S. Cl. ........................ 424/9.1; 424/1.11; 600/101; 606/45
(58) Field of Search ................................ 424/1.11, 9.1, 424/1.65, 9.2; 600/101, 103, 104, 184, 920; 502/180; 606/45; 423/449.1

(56) References Cited

U.S. PATENT DOCUMENTS 6,280,702 B1 * 8/2001 Carter et al. ................. 424/9.1

\* cited by examiner

Primary Examiner—Dameron L. Jones
(74) Attorney, Agent, or Firm—Eugene Chovanes

(57) ABSTRACT

An endoscopic stain is provided that includes a carbon pigment and a suspending/viscosity-increasing agent in a pharmaceutically acceptable delivery vehicle, wherein the carbon pigment has a total level of polycyclic aromatic hydrocarbons (PAH) of not greater than 0.5 ppm. Methods of staining an internal site utilizing the stain of the invention and kits that include the stain of the invention are also provided.

22 Claims, No Drawings

ENDOSCOPY TISSUE STAIN

This application is a continuation-in-part application of application Ser. No. 09/303,164 filed on Apr. 30, 1999, issued as U.S. Pat. No. 6,280,702.

BACKGROUND OF INVENTION

The invention relates to a permanent stain for marking of internal sites for endoscopic identification, e.g., in the gastrointestinal tract, bladder, or lungs. The invention also includes a method and kit for marking of the sites.

At present, there is an absence of FDA approved marking compositions formulated especially for use in endoscopy for the staining of internal sites in the body. Endoscopists have had to make do by adapting their techniques to use commercially available writing inks and other standard stains which are not approved for use in humans. Available approved stains are not permanent markers.

Endoscopic stains including Lugol's solution, methylene blue, toluidine blue, congo red, phenol red, indigo carmine and India ink are described by the American Society for Gastrointestinal Endoscopy (ASGE) in *Technology Assessment Status Evaluation, Endoscopic Tissue Staining and Tattooing*, published by American Society for Gastrointestinal Endoscopy, Manchester, Mass., October 1995. The only known permanent stain for endoscopic tattooing is India ink. The use of India ink to endoscopically label colonic lesions was first described by J. L. Ponsky and J. F. King, *Gastrointest Endosc.* 1975, 22:42–3. India ink has also been used for marking esophageal lesions as described by R. T. Shaffer et al., *Gastrointest. Endosc.* 1998, 47:257–260.

It was found that other permanent fountain pen inks are not an acceptable substitute for commercially available India ink. E. L. Goldman, *Internet Medicine News*, Feb. 1, 1997, p. 50.

The compositions of various commercially available India inks and comparisons of their use in endoscopic tattooing of the colon have been described by P. S. Salomon et al., *Gastrointest. Endosc.* 1991, 39(6): 803–804. The composition of India ink made by Higgins (Faber-Castell, Lewisberg, Tenn.) is described as containing about 7% carbon pigment, 5% propylene glycol and smaller concentrations of shellac, ammonium hydroxide and surfactant and when the composition was diluted in equal parts (50:50) with bacteriostatic water, it caused an inflammatory response. The composition of India ink made by Pelikan (Hanover, Germany) is described as containing ethylene glycol, sodium tetraborate decahydrate, ammonia and gelatin, and when diluted in 1:10 dilution in sterile water, it caused an abscess. India ink made by Koh-I-Noor (Bloomsburg, N.J.) is described as composed of carbon particles (approximately 7% by weight) with stabilizing diluents present in all commercial products, including ethylene glycol methyltert-butyl ether (Methyl Carbitol), phenol, ammonium hydroxide and shellac, and was diluted 1:100 with 0.9% normal saline solution and successfully tested by Salomon et al. An attempt by Salomon et al. to test a "homemade" India ink of dry carbon pigment, 0.1% by weight mixed with normal saline solution was unsuccessful.

Although some endoscopists have found small volumes of India ink for tattooing of the colon to be safe (see, e.g., B. A. Shatz, *Gastrointest. Endosc.* 1997, 45(2): 153–156), others have found complications following colonoscopic India ink injection. V. A. Botoman et al. 1994, *Dis. Colon Rectum* 37:775–776; J. Lightdale, *Gastrointest. Endosc.* 1991, 37(1): 99–100; S. I. Park et al., *Gastrointest. Endosc.* 1991, 37(1): 68–70.

Following reports of complications using India ink, some have looked for alternatives. A pure suspension of charcoal was tested for colonoscopic tattoo, using 5% weight/volume aqueous suspension of micronized charcoal particles. S. Naveau et al. 1991, *Gastrointest. Endosc.* 1991, 37(6): 624–25. Indocyanine green was also used for the marking of lesions of the colon by D. C. Hammond, et al., *The American Surgeon* 1993, 59(3): 205–210, but this stain does not have long term permanence. Problems still remain in endoscopic tissue marking.

It is an object of the invention to provide an improved endoscopic tissue staining composition for permanent marking of internal sites in the body. It is a further object of the invention to provide a staining composition which can be used at internal sites with no adverse effects.

SUMMARY OF THE INVENTION

An endoscopic tissue staining composition comprises carbon pigment and a suspending/viscosity-increasing agent in a pharmaceutically acceptable delivery vehicle. The total level of polycyclic aromatic hydrocarbons is not greater than 0.5 ppm. Preferred suspending/viscosity-increasing agents include glycerol, propylene glycol, isopropylene glycol, polyethylene glycol or cellulose. A preferred delivery vehicle includes water.

Also in a preferred embodiment, the composition includes a surfactant. Preferred surfactants include polyoxyethylene sorbitan esterified with fatty acid. In another preferred embodiment, the composition includes an anti-foaming agent. Preferred anti-foaming agents include dimethicone or simethicone.

An embodiment of the invention includes a composition comprising carbon particles, suspending/viscosity-increasing agent, anti-foaming agent and surfactant, respectively in internal staining, suspending/viscosity-increasing, anti-foaming and surface-active amounts, prepared in a pharmaceutically acceptable vehicle, preferably water. The carbon preferably includes amorphous carbon powders such as carbon black and activated or unactivated (nonactivated) carbon. Carbon is "activated" by heating to about 800–900° C. resulting in a porous internal structure. "Unactivated" carbon is not treated this way. Preservative may also be added in anti-microbial amounts.

In a particularized embodiment, the composition comprises:

0.01% to 1.0% carbon, preferably 0.1% to 1.0%,

5% to 25% suspending/viscosity-increasing agent, preferably 10% to 20%, 0.005% to 0.05% anti-foaming agent, preferably 0.01% to 0.04%, 0.5% to 1.5% surfactant, preferably 0.75%to 1.25%, zero to 2.0% preservative, preferably 0.5% to 1.5%, and sufficient water, for example, about 70% to 90%, for a 100% composition.

All percentages herein are based on weight. The carbon is carbon black, activated or unactivated carbon.

In a preferred embodiment, the suspending/viscosity-increasing agent is glycerol, the anti-foaming agent is simethicone, the surfactant is esterified polyoxyethylene sorbitan, and the anti-microbial is benzyl alcohol. Therefore this embodiment of the invention comprises:

0.01% to 1.0% carbon, preferably 0.01% to 1.0%,

5% to 25% glycerol, preferably 10% to 20%, 0.005% to 0.05% simethicone, preferably 0.01% to 0.04%, 0.5% to 1.5% polyoxyethylene sorbitan esterified with fatty acid, preferably 0.75% to 1.25%, zero to 2.0% benzyl alcohol, preferably 0.5% to 1.5%, and sufficient water for a 100% composition.

The composition is used for marking internal sites, e.g., in the gastrointestinal tract, urinary bladder or bronchi.

A method for marking or tattooing of internal sites, e.g., in the gastrointestinal tract, urinary bladder or lungs for endoscopic identification includes injecting a staining amount of the composition of the invention comprising carbon black in a pharmaceutically acceptable delivery vehicle such as water. In another embodiment, the injected composition includes carbon, humectant, anti-foaming agent and surfactant, respectively in staining, wetting, anti-foaming, and surface-active amounts, injected in proximity to the site. Preferred embodiments for the method utilize the compositions of the inventions described above.

In a particular embodiment, the method for marking internal sites comprises injecting the site with a composition comprising:

0.01% to 1.0% carbon, preferably 0.01% to 1.0%,

5% to 25% suspending/viscosity-increasing agent, preferably 10% to 20%, 0.005% to 0.05% anti-foaming agent, preferably 0.01% to 0.04%, 0.5% to 1.5% surfactant, preferably 0.75% to 1.25%, zero to 2.0% preservative, preferably 0.5% to 1.5%, and sufficient water, for example, about 70% to 90%, for a 100% composition.

The carbon is carbon black, activated or unactivated carbon.

In a preferred embodiment for a method of marking internal sites, the suspending/viscosity-increasing agent is glycerol, the anti-foaming agent is simethicone, the surfactant is esterified polyoxyethylene sorbitan, and the anti-microbial is benzyl alcohol. Therefore this embodiment of the method of the invention includes injecting a composition comprising:

0.01% to 1.0% carbon, preferably 0.1% to 1.0%,

5% to 25% glycerol, preferably 10% to 20%, 0.005% to 0.05% simethicone, preferably 0.01% to 0.04%, 0.5% to 1.5% polyoxyethylene sorbitan esterified with fatty acid, preferably 0.75% to 1.25%, zero to 2.0% benzyl alcohol, preferably 0.5% to 1.5%, and sufficient water for a 100% composition.

Injection may be made, for example, tangentially to a site, proximally and distally to a site, or in all four quadrants of the lumen around the site. The total amount to be injected can be determined by the skilled artisan and can be, for example, from about 0.5 ml to about 5.0 ml.

A kit for endoscopic tissue staining or tattooing of internal sites, e.g., in the gastrointestinal tract, urinary bladder or lungs, includes the composition of the invention which comprises carbon particles in a pharmaceutically acceptable delivery vehicle such as water, packaged with a means for endoscopic injection.

An embodiment of the kit includes a composition comprising carbon particles, suspending/viscosity-increasing agent, anti-foaming agent and surfactant, respectively in staining, suspending/viscosity-increasing, anti-foaming, and surface-active amounts, containerized and packaged with a means for endoscopic injection.

In a particular embodiment, the kit includes a composition comprising:

0.01% to 1.0% carbon, preferably 0.1% to 1.0%,

5% to 25% suspending/viscosity-increasing agent, preferably 10% to 20%, 0.005% to 0.05% anti-foaming agent, preferably 0.01% to 0.04%, 0.5% to 1.5% surfactant, preferably 0.75% to 1.25%, zero to 2.0% preservative, preferably 0.5% to 1.5%, and sufficient water for a 100% composition.

The carbon is carbon black, activated or unactivated carbon. A preferred means for injection includes a syringe and sclerotherapy needle. A catheter is also useful for reaching internal sites.

More preferably, the kit includes the composition of the invention as described above wherein the suspending/viscosity-increasing agent is glycerol, the anti-foaming agent is simethicone, the surfactant is esterified polyoxyethylene sorbitan, and the anti-microbial is benzyl alcohol, and the composition comprises:

0.01% to 1.0% carbon, preferably 0.1% to 1.0%,

5% to 25% glycerol, preferably 10% to 20%, 0.005% to 0.05% simethicone, preferably 0.01% to 0.04%, 0.5% to 1.5% polyoxyethylene sorbitan esterified with fatty acid, preferably 0.75% to 1.25%, zero to 2.0% benzyl alcohol, preferably 0.5% to 1.5%, and sufficient water for a 100% composition.

The composition is containerized and packaged with a syringe, sclerotherapy needle and catheter, to be used in conjunction with an endoscope, sigmoidoscope or colonoscope.

Advantageously, the composition of the invention is free of toxins and antigens, and is inert and safe for use in humans, has high contrast and low viscosity, and resists diffusion when injected.

DETAILED DESCRIPTION OF THE INVENTION

An endoscope traditionally includes a bundle of light transmitting fibers in conjunction with a telescopic lens system so that the device has an image receiving end and an insertion end. Currently, more advanced video systems are used in which an optically sensitive chip collects the image and presents an image on a video screen via computer digital technology. An endoscopist or surgeon can examine internal body tissues by guiding the insertion tube end to the desired location in the body and observing through the viewing end, or more commonly on a viewing screen via computer digital technology. Endoscopes are available for various specialized purposes. For example, there are upper endoscopes for examining the esophagus, stomach and duodenum, urethroscopes for examining the urethra and bladder, colonoscopes for examining the colon, angioscopes for examining the blood vessels and heart, bronchoscopes for examining the bronchi, laparoscopes for examining the joint spaces, and sigmoidoscopes for examining the rectum and sigmoid colon. Endoscopes can also include channels for delivery of air, liquid and suction, biopsy instruments, graspers and other instruments. Endoscopes are known in the art and described, for example, in U.S. Pat. Nos. 5,681,262, 5,025,778, 4,748,970, 4,468,216 and 4,146,019.

When a cancer is found in the gastrointestinal tract, urinary bladder or bronchi of the lungs, marking of the site is used to guide the surgeon to the site. Moreover, polyps in the colon are generally promptly removed because of their potential for malignancy. Polyps are discrete mass lesions that protrude into the intestinal lumen. Mucosal neoplastic (adenomatous) polyps give rise to adenocarcinoma of the colon and therefore, polyps detected at sigmoidoscopy or barium enema are removed as soon as possibly by colonoscopic polypectomy or other techniques such as those described in U.S. Pat. Nos. 5,122,147 and 5,542,948. Sometimes polyps or tumors cannot be safely or completely removed by colonoscopy, and surgical resection must follow. Once the polyps have been removed, surveillance colonoscopy is periodically repeated to look for missed polyps, new adenomas, residual or recurrent cancer.

Cancerous lesion sites or potentially cancerous lesion sites are marked because on follow-up it can be difficult to localize the lesion sites. Therefore, a marking composition must be relatively permanent to enable the surgeon to find the exact site at a later time.

It has been discovered that the disadvantages of India ink can be overcome by using a composition comprising carbon particles as pigment in a pharmaceutically acceptable carrier. Another embodiment of the invention includes carbon, suspending/viscosity-increasing agent, anti-foaming agent and surfactant, and the carbon is carbon black, activated or unactivated carbon. Carbon black, activated and unactivated carbon are amorphous forms of carbon and are described, for example, in the *Kirk-Othmer Concise Encyclopedia of Chemical Technology*, D. Eckroth et al. ed., John Wiley & Sons, New York 1985, at pages 204–209. Amorphous forms of carbon, i.e., carbon forms which are poorly developed in crystallinity, include carbon black, coke and charcoal. These all can be used in the form of particles or powder but differ in the manner in which they are made.

Carbon black is finely divided carbon such as vaporized heavy oil fractions produced by burning hydrocarbons using partial oxidation. The pigment can contain over 97% carbon. The oil furnace process represents the most widely used method for producing carbon black. Generally, a liquid hydrocarbonaceous feedstock is sprayed into turbulent products of combustion produced by reacting fluid fuel and oxygen and the hydrocarbon feedstock is converted into carbon black which is separated from combustion gases. Carbon black can also be produced by burning natural gas and letting the flame impinge on a cool surface.

The preferred carbon pigment useful herein is low in incompletely burned hydrocarbons which may be absorbed during manufacture; particularly, the carbon pigment is low in aromatics and other compounds which may be carcinogens. More particularly, the preferred carbon pigment is low in residual polycyclic aromatic hydrocarbons (PAH). By "low" is meant not greater than 0.5 ppm. As shown in Example 2, conventional endoscopic stains contain PAH levels well above the level present in the endoscopic stain of the invention.

It is also preferred that the endocscopic tissue stain of the invention be non-cytotoxic. Conventional tissue stains are cytotoxic due to, for example, various toxic impurities. As defined herein, non-cytotoxic means a score of 2 or less based upon the United States Pharmacopoeia (USP) Cytotoxicity test. As shown in Example 3, the tissue stain of the invention is below the level considered cytotoxic, while conventional tissue stains are above the level considered cytotoxic.

Charcoal is prepared by the ignition of wood, sugar, and other carbon-containing compounds in the absence of air. It has a graphitic structure but is not well developed in crystallinity. It will therefore be categorized as amorphous herein. Activated carbon is similarly obtained by the carbonization or destructive distillation of vegetable matter, e.g., wood, nut shells, bones, or other carbonaceous material. The carbon is activated by heating to high temperatures in the presence of water or carbon dioxide which results in a carbon having a porous internal structure. Carbon which has not been subjected to this treatment will be called unactivated herein. Coke is prepared by heating coal in the absence of air.

In addition to carbon pigment, the composition includes a suspending or viscosity-increasing agent. Suspending or viscosity-increasing agents increase viscosity and keep the carbon in solution. Suspending/viscosity-increasing agents include Acacia, Agar, Alginic Acid, Aluminum Monosterate, Attapulgite-Activated, Attapulgite-Colloidal Activated, Bentonite, Bentonite-Purified, Bentonite-Magma, Carbomer 910, Carbomer 934, Carbomer 934P, Carbomer 940, Carbomer 941, Carbomer 1342, Carboxymethylcellulose Calcium, Carboxymethylcellulose Sodium, Carboxymethylcellulose Sodium 12, Carrageenan, Cellulose: Microcrystalline and Carboxymethylcellulose Sodium, Dextrin, Gelatin, Guar Gum, Hydroxyethyl Cellulose, Hydroxypropyl Cellulose, Hydroxypropyl Methylcellulose, Magnesium Aluminum Silicate, Methylcellulose, Pectin, Polyethylene Oxide, Polyvinyl Alcohol. Povidone, Propylene Glycol Alginate, Silicon Dioxide, Silicon Dioxide-Colloidal, Sodium Alginate, Tragacanth, and Xanthan Gum. Other agents to increase viscosity and keep the carbon particles in solution include as non-limiting examples emulsifying or solubilizing agents including Acacia, Cholesterol, Diethanolamine (Adjunct), Glyceryl Monostearate, Lanolin Alcohols, Lecithin, Mono-and Di-glycerides, Monoethanolamine (Adjunct), Oleic Acid (Adjunct), Oleyl Alcohol (Stabilizer), Poloxamer, Polyoxyethlene 50 Stearate, Polyoxyl 35 Castor Oil, Polyoxyl 40 Hydrogenated Castor Oil, Polyoxl 10 Oleyl Ether, Polyoxyl 20 Cetostearyl Ether, Polyoxyl 40 Stearate, Polysorbate 20, Polysorbate 40, Polysorbate 60, Polysorbate 80, Propylene Glycol Diacetate, Propylene Glycol Monostearate, Sodium Lauryl Sulfate, Sodium Stearate, Sorbitan Monolaurate, Sorbitan Monooleate, Sorbitan Monopalmitate, Sorbitan Monostearate, Stearic Acid, Trolamine, and Wax-Emulsifying. Preferred agents include as non-limiting examples, glycerine (glycerol), propylene glycol, isopropylene glycol, polyethylene glycol and cellulose. Other compatible agents listed in the United States Pharmacopia can also be used. In one embodiment, a preferred suspending or viscosity-increasing agent is glycerol (propane-1,2,3-triol or glycerin) which is a trihydric alcohol soluble in water and alcohol. Preferred is USP (pharmaceutical grade).

In a preferred embodiment, the composition further includes a surfactant. A preferred surfactant is a non-ionic surfactant which is a polyoxyethylene sorbitan ester obtained by esterification of sorbitol with fatty acid, e.g., monolaurate, monooleate, monopalmitate, monostearate, trioleate and tristearate. Compounds of this type are commercially available as Tweens (20, 21, 40, 60, 65, 80, 80R, 85) (ICI American, Wilmington, Del.). Tween 80 is preferred.

In a preferred embodiment, the composition further includes an anti-foaming agent. Preferred anti-foaming agents are dimethicone and simethicone. Simethicone (USP) is described in the USP Dictionary of USAN and International Drug Names, U.S. Pharmacopeia, Rockville, Md., 1997 at page 652 as a mixture of poly(dimethylsiloxane) and silicon dioxide. The poly(dimethylsiloxane) and silicon dioxide. The poly (dimethylsiloxane) is α-(trimethylsilyl)-ω-methyl-poly[oxy (dimethylsilylene)]. The calculated average of dimethylsiloxane units in poly(dimethylsilylene) is 200 to 350. The simethicone is preferably supplied from the USP or FDA acceptable solution.

It is preferred that the surfactant and the anti-foaming agent are substantially non-irritating and biocompatible. Biocompatible as used herein means non-damaging to human tissue.

The composition may also include a suitable preservative such as benzyl alcohol, methyl or ethyl paraben, or benzalkonium chloride, which can function as an antimicrobial.

Other pharmaceutically acceptable excipients may be added, e.g., buffers such as citrate or phosphate buffering agents.

The composition is prepared by mixing the components in a pharmaceutically acceptable vehicle suitable for internal injection such as water, and preferably sterilizing by known methods, e.g., autoclaving, or radiation, or the components may be sterilized separately before mixing. The composition has a sufficiently low viscosity to allow injection through a long transendoscopic catheter such as a sclerotherapy needle.

The composition is used in the form of a liquid surgical marker for endoscopic marking (tattooing) using known endoscopic techniques. For example, the liquid surgical marker can be drawn into a syringe and injected through a sclerotherapy needle long enough to traverse a colonoscope. As non-limiting examples, marking may be done by injecting under the mucosa by oblique penetration once, proximally and distally, or at four quadrants in proximity to the lesion using the tangential 4-quadrant technique.

EXAMPLE 1

An endoscopic staining composition is prepared by combining:

0.2% carbon black,
15% glycerol,
0.02% simethicone,
1.0% polyoxyethylene sorbitan esterified with monooleate (Tween 80), and
1.0% benzyl alcohol; and sterile water for injection.

The composition is endoscopically injected to mark the site of a cancerous or pre-cancerous lesion on the internal mucosa. As a non-limiting example, staining at the internal site can be accomplished with 0.1 to 1 ml per injection site. Placement of the stain is confirmed visually at the injection site as the black stain spreads in the submucosa layer. A kit includes the composition packaged with a syringe and sclerotherapy needle or catheter.

EXAMPLE 2

An endoscopic marker of the invention and a conventional endoscopic stain (Higgins Ink) were analyzed for their level of PAH.

Total PAH for the two samples were determined. Both ink samples were extracted into methylene chloride. Total PAH level was determined by Gas Chromatography-Flame Ionization Detection and GC-Mass Spectrometry-Single Ion Monitoring (Hewlett-Packard).

The results of the analysis indicate that the endoscopic stain of the invention has a total PAH concentration of less than 0.1 ppm. The conventional ink, on the other hand, demonstrated a total PAH level of at least 0.8 ppm or higher.

EXAMPLE 3

The cytotoxicity of a stain of the invention (SPOT) was compared against two conventional stains (Higgins India Ink and Speedball Super Black India Ink).

The samples were analyzed according to the requirements of the U.S. Pharmacopoeia (USP) Cytotoxicity Test. The reactivity grades are set forth in Table 1 as listed in the USP/National Formulary, Current Edition.

TABLE 1

Reactivity Grades for Elution Test

| Grade | Reactivity | Conditions of all Cultures |
|---|---|---|
| 0 | None | Discrete intracytoplasmic granules; no cell lysis. |
| 1 | Slight | Not more than 20% of the cells are round, loosely attached, and without intracytoplasmic granules; occasionally lysed cells are present. |
| 2 | Mild | Not more than 50% of the cells are round and devoid of intracytoplasmic granules; extensive cell lysis and empty areas between cells. |
| 3 | Moderate | No more than 70% of the cell layers contain rounded cells and/or are lysed. |
| 4 | Severe | Nearly complete destruction of the cell layers. |

The requirements of the USP are met if the cell culture exposed to the sample extract is not greater than Grade 2, which is a mild reactivity. Therefore, a level above 2 is considered cytotoxic and a level of 2 or lower is considered non-cytotoxic.

The samples were extracted for 24 hours at 37° C., 5% $CO_2$. 0.1 ml of each sample was then transferred directly to duplicate monolayer plates containing 2 ml of the MEM test media containing mouse embryo cells (L929). The test plates had a concentration of approximately $2 \times 10^5$ cells per plate. The plates were permitted a reaction time of 48 hours. Polypropylene was used as a negative control. Sterile latex rubber was used as a positive control. This procedure was then duplicated to obtain two cytotoxicity readings for each sample.

The results from the cytotoxicity test are set forth in Table 2.

TABLE 2

| Sample | Sample Score | Negative Ctrl. Score | Positive Ctrl. Score | Test Blank |
|---|---|---|---|---|
| 1) SPOT | 1/1 | 0/0 | 4/4 | Normal Cells |
| 2) Higgins India Ink | 3/3 | 0/0 | 4/4 | Normal Cells |
| 3) Speedball India Ink | 3/3 | 0/0 | 4/4 | Normal Cells |

As shown in Table 2, the stain of the invention scored 1/1 indicating a non-cytotoxic stain, while conventional stains scored above 2 indicated these conventional stains are cytotoxic.

What is claimed is:

1. An endoscopic tissue staining composition comprising a carbon pigment and a suspending/viscosity-increasing agent in a pharmaceutically acceptable delivery vehicle, wherein said carbon pigment has a level of total polycyclic aromatic hydrocarbons of not greater than 0.5 ppm.

2. A composition as set forth in claim 1 wherein said composition is non-cytotoxic.

3. A composition as set forth in claim 1 wherein the suspending/viscosity-increasing agent comprises glycerol, propylene glycol, isopropylene glycol, polyethylene glycol or cellulose.

4. A composition as set forth in claim 1 wherein said composition further comprises a surfactant.

5. A composition as set forth in claim 4 wherein said surfactant comprises polyoxyethylene sorbitan esterified with fatty acid.

6. A composition as set forth in claim 1 wherein said composition further comprises an anti-foaming agent.

7. A composition as set forth in claim 6 wherein said anti-foaming agent comprises dimethicone or simethicone.

8. A composition as set forth in claim 1 wherein the delivery vehicle comprises water.

9. A composition as set forth in claim 1 wherein the carbon pigment comprises particles of carbon black, activated carbon or unactivated carbon.

10. An endoscopic tissue staining composition comprising
    a carbon pigment,
    a suspending/viscosity-increasing agent,
    a surfactant, and
    an anti-foaming agent;
        in a pharmaceutically acceptable delivery vehicle, wherein said carbon pigment has a level of total polycyclic aromatic hydrocarbons of not greater than 0.5 ppm.

11. A composition as set forth in claim 10, said composition comprising:
    about 0.01% to about 1.0% carbon pigment,
    about 5.0% to about 25% suspending/viscosity-increasing agent,
    about 0.005% to about 0.05% anti-foaming agent,
    about 0.5% to about 1.5% surfactant, and
    water as a delivery vehicle to yield 100% composition based on weight.

12. A composition as set forth in claim 11 wherein the suspending/viscosity-increasing agent comprises glycerol, propylene glycol, isopropylene glycol, polyethylene glycol or cellulose, the anti-foaming agent comprises dimethicone or simethicone, and the surfactant comprises polyoxyethylene sorbitan esterified with fatty acid.

13. A composition as set forth in claim 10 comprising:
    about 0.1% to about 10% carbon pigment,
    about 10% to about 20% suspending/viscosity-increasing agent,
    about 0.0 1% to about 0.04% anti-foaming agent,
    about 0.5% to about 1.5% surfactant, and
    water to yield 100% composition based on weight.

14. A composition as set forth in claim 13 wherein the suspending/viscosity-increasing agent comprises glycerol, propylene glycol, isopropylene glycol, polyethylene glycol or cellulose, the anti-foaming agent comprises dimethicone or simethicone, and the surfactant comprises polyoxyethylene sorbitan esterified with fatty acid.

15. An endoscopic staining composition as set fourth in claim 11, said composition comprising:
    about 0.01% to about 1.0% carbon pigment,
    about 5% to about 25% glycerol,
    about 0.005% to about 0.05% simethicone,
    about 0.5% to about 1.5% polyoxyethylene sorbitan esterified with fatty acid,
    zero to about 2.0% benzyl alcohol, and
    sufficient water for a 100% composition.

16. A method for staining of an internal site comprising injecting the composition of claim 1 in a staining amount in proximity to the site.

17. A method as set forth in claim 16 wherein the internal site is in the gastrointestinal tract, urinary bladder or lungs.

18. A method for staining of an internal site comprising injecting the composition of claim 14 in a staining amount in proximity to the site.

19. A method as set forth in claim 18 wherein the internal site is in the gastrointestinal tract, urinary bladder or lungs.

20. A kit comprising the composition of claim 1 packaged with a means for endoscopic injection.

21. A kit comprising the composition of claim 10 packaged with a means for endoscopic injection.

22. A kit as set forth in claim 20 wherein the means for endoscopic injection comprises a syringe and sclerotherapy needle.

* * * * *